US00PP23133P3

(12) United States Plant Patent
Klemm et al.

(10) Patent No.: US PP23,133 P3
(45) Date of Patent: Oct. 23, 2012

(54) POT CARNATION PLANT NAMED 'KLEDP10105'

(50) Latin Name: *Dianthus caryophyllus*
Varietal Denomination: KLEDP10105

(75) Inventors: Nils Klemm, Stuttgart (DE); Martin Glawe, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 13/065,482

(22) Filed: Mar. 23, 2011

(65) Prior Publication Data

US 2012/0246773 P1 Sep. 27, 2012

(51) Int. Cl.
*A01H 5/00* (2006.01)

(52) U.S. Cl. ..... Plt./276

(58) Field of Classification Search ..... Plt./276
See application file for complete search history.

*Primary Examiner* — Kent L Bell
(74) *Attorney, Agent, or Firm* — Jondle & Associates, P.C.

(57) ABSTRACT

A new variety of Carnation named 'KLEDP10105' particularly characterized by its compact growth habit, good branching, early flowering, and salmon pink flowers with light purple centers, is disclosed.

1 Drawing Sheet

Genus and species: *Dianthus caryophyllus*.
Variety denomination: 'KLEDP10105'.

BACKGROUND OF THE NEW PLANT

The present invention comprises a new and distinct variety of Carnation, botanically known as *Dianthus caryophyllus*, and hereinafter referred to by the variety name 'KLEDP10105'. 'KLEDP10105' originated as a naturally occurring mutation of 'Oscar' (unpatented) discovered in Latina, Italy in April 2009. A single plant selection with salmon pink flowers was subsequently chosen for further evaluation and asexual propagation.

The new variety was first propagated via vegetative cuttings in April 2009 in Stuttgart, Germany and has been asexually reproduced repeatedly by vegetative cuttings in Stuttgart, Germany for approximately three to four generations. 'KLEDP10105' has been found to retain its distinctive characteristics through successive asexual propagations via vegetative cuttings.

Plant Breeder's Rights for this variety were applied for in Canada on Mar. 19, 2010. 'KLEDP10105' has not been made publicly available or sold more than one year prior to the filing date of this application.

SUMMARY OF THE INVENTION

The following are the most outstanding and distinguishing characteristics of this new variety when grown under normal horticultural practices in a glass greenhouse in Stuttgart, Germany.

1. Compact growth habit;
2. Good branching;
3. Early flowering; and
4. Salmon pink flowers with light purple centers.

DESCRIPTION OF THE PHOTOGRAPH

This new Carnation plant is illustrated by the accompanying photograph which shows the overall plant habit including blooms and foliage of the plant. The colors shown are as true as can be reasonably obtained by conventional photographic procedures. The photograph was taken in April 2010 of a 5-month old plant grown from rooted cuttings in a 10 centimeter pot in a glass greenhouse in Stuttgart, Germany under normal horticultural practices.

DESCRIPTION OF THE NEW VARIETY

The following detailed descriptions set forth the distinctive characteristics of 'KLEDP10105'. The data which define these characteristics were collected from asexual reproductions carried out in Stuttgart, Germany. The plant history was taken in Spring 2010 on 5-month old plants grown in 10 centimeter pots with a minimum pinch date of 45 weeks. The plants were grown in a greenhouse covered with glass. The color readings were determined under natural light. Color references are to The R.H.S. Colour Chart of The Royal Horticultural Society of London (R.H.S.), Fifth Edition (2007).

DETAILED BOTANICAL DESCRIPTION OF THE NEW PLANT

Classification:
- *Family*.—Caryophyllaceae.
- *Genus and species*.—*Dianthus caryophyllus*.
- *Common name*.—Carnation.

Plant:
- *Form*.—Potted plant.
- *Habit*.—Upright.
- *Height* (*from top of soil*).—12.0 cm.
- *Width* (*spread*).—14.0 cm.
- *Life cycle*.—Seasonal.
- *Flowering habit*.—Continuous.
- *Time to produce a finished flowering plant*.—4 months.
- *Propagation type*.—Vegetative cuttings.
- *Time to initiate roots*.—16 days.
- *Root description*.—White, fine.
- *Temperature tolerances*.—Normal.

Branches:
*Quantity per plant.*—6 to 8.
*Color.*—RHS 138A.
*Length.*—4.0 cm to 6.0 cm.
*Diameter.*—0.5 cm.
*Internode length.*—0.2 cm to 0.3 cm.
*Texture.*—Smooth.

Leaves:
*Arrangement.*—Opposite.
*Shape.*—Lanceolate.
*Apex.*—Acute.
*Base.*—Obtuse.
*Margin.*—Entire.
*Color.*—Immature leaf (both upper and lower surfaces): RHS 139C. Mature leaf (both upper and lower surfaces): RHS 138B.
*Size.*—Length: 2.5 cm to 4.0 cm. Width: 0.8 cm.
*Texture.*—Smooth.
*Venation color.*—Upper surface: RHS 139C. Lower surface: RHS 139D.
*Petioles.*—Absent.

Flowers:
*Type.*—Small sprays.
*Flowering season.*—Spring to Fall.
*Lastingness of the inflorescence.*—12 to 16 days.
*Size.*—Width: 3.5 cm. Depth: 1.5 cm.
*Shape.*—Round.
*Fragrance.*—Present.
*Number of flowers per plant.*—6 to 8.
*Calyx.*—Form: Cylinder vase. Length: 1.8 cm. Width: 0.8 cm.

Flower buds:
*Color.*—RHS 137B.
*Shape.*—Elliptic.
*Length.*—1.6 cm.
*Diameter.*—0.6 cm.

Petals:
*Arrangement.*—Arranged in several whorls.
*Quantity* (*per flower*).—Greater than 18 to 25.
*Shape.*—Spoon-shaped.
*Apex.*—Obtuse.
*Base.*—Acute.
*Margin.*—Entire.
*Size.*—Length: 2.0 cm. Width: 1.4 cm.
*Color.*—When opening: Upper surface: RHS 55A with RHS 54A centers. Lower surface: RHS 55C. When fully opened: Upper surface: RHS 55C with RHS 54A centers. Lower surface: RHS 55D.
*Texture* (*both upper and lower surfaces*).—Smooth.

Sepals:
*Arrangement.*—Fused.
*Quantity* (*per flower*).—4.
*Shape.*—Elliptic.
*Apex.*—Acute.
*Base.*—Obtuse.
*Margin.*—Smooth.
*Size.*—Length: 0.6 cm. Width: 0.5 cm.
*Color.*—Upper surface: RHS N138B to RHS N138C. Lower surface: RHS 138B to RHS 138C.
*Texture* (*both upper and lower surfaces*).—Smooth.

Pedicel
*Length.*—0.1 cm to 0.5 cm.
*Diameter.*—1.0 mm.
*Color.*—RHS N138B.

Peduncle:
*Length.*—5.0 cm to 8.0 cm.
*Diameter.*—0.2 cm to 0.3 cm.
*Texture.*—Smooth.
*Color.*—RHS 138A.

Reproductive organs:
*Pistils.*—Quantity: 1. Style length: 1.5 cm. Style color: RHS 49D. Stigma color: RHS 49D. Ovary shape: Elliptic to cylindric. Ovary length: 0.5 cm to 0.7 cm. Ovary color: RHS 138C.
*Stamens.*—Quantity: Moderate. Length: 0.5 cm to 0.8 cm. Filament: Length: 0.4 cm to 0.6 cm. Color: RHS NN155D. Anther color: RHS 49D. Pollen: Amount: Moderate. Color: RHS 49D.

Fruit and seed set: None observed.
Cold hardiness: Hardy to −5° Celsius.
Disease and insect resistance: Very good tolerance to disease.

COMPARISON WITH PARENTAL AND COMMERCIAL VARIETIES

'KLEDP10105' differs from the parental variety 'Oscar' (unpatented) in that 'KLEDP10105' has salmon pink flowers, while 'Oscar' has purple pink flowers. 'KLEDP10105' differs from the commercial variety 'CFPC Cheerful' (U.S. Plant Pat. No. 21,365) in that 'KLEDP10105' has salmon pink flowers (RHS 55C), an upright growth habit, and round-shaped flowers, while 'CFPC Cheerful' has red flowers (RHS 46C), a semi-upright growth habit, and dome-shaped flowers.

We claim:

1. A new and distinct variety of Carnation plant named 'KLEDP10105' as shown and described herein.

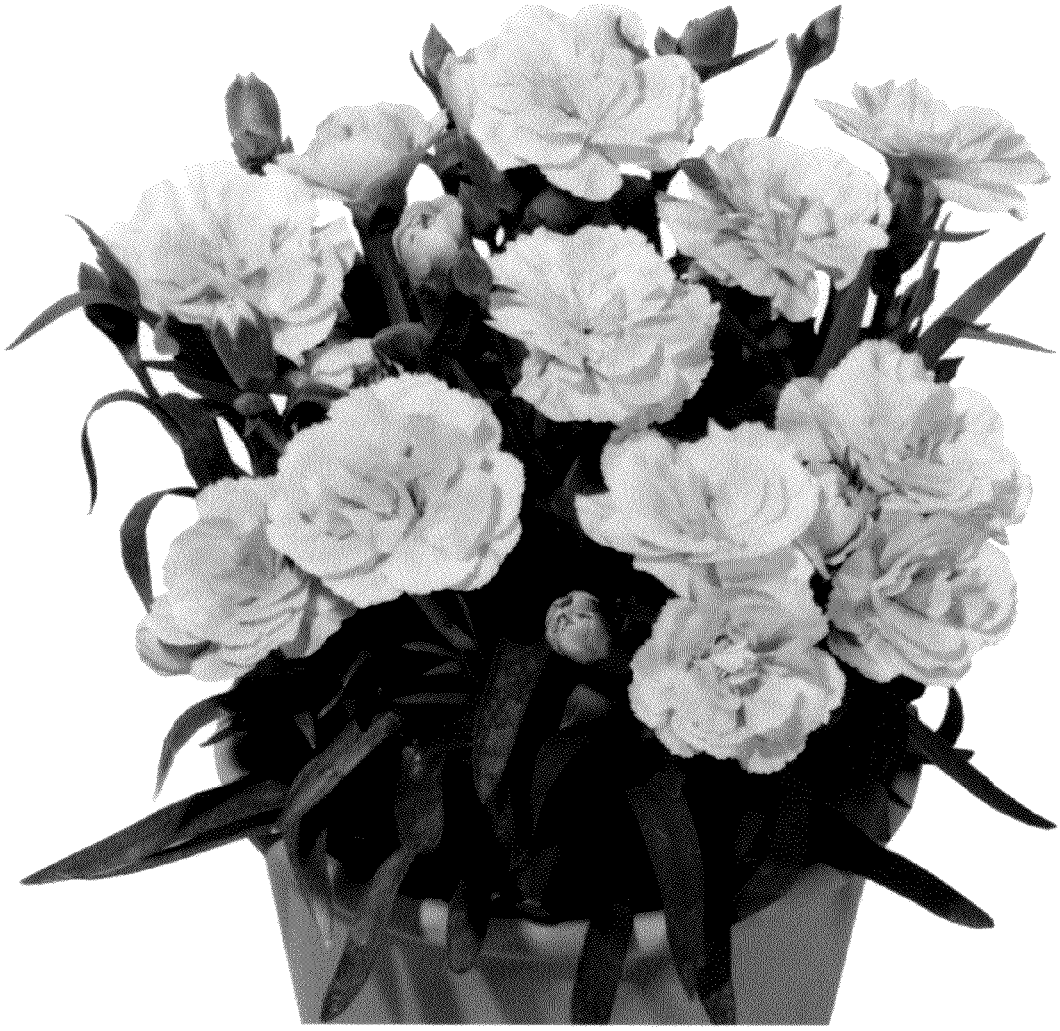

* * * * *